(12) United States Patent
Batra et al.

(10) Patent No.: US 7,052,859 B2
(45) Date of Patent: May 30, 2006

(54) MUCIN 4 EXPRESSION AS A MARKER FOR PANCREATIC CANCER

(75) Inventors: Surinder K. Batra, Omaha, NE (US); Randall E Brand, Omaha, NE (US); Jöerg Ringel, Rostoct (DE); Grit Faulmann, Leipzig (DE); Matthias Löhr, Weinheim (DE); Grish C. Varshney, Chandigarh (IN)

(73) Assignee: The Board of Regents of the University of Nebraska, Omaha, NE (US)

( * ) Notice: Subject to any disclaimer, the term of this patent is extended or adjusted under 35 U.S.C. 154(b) by 116 days.

(21) Appl. No.: 10/279,454

(22) Filed: Oct. 24, 2002

(65) Prior Publication Data

US 2003/0134343 A1 Jul. 17, 2003

Related U.S. Application Data

(62) Division of application No. 09/733,444, filed on Dec. 8, 2000, now Pat. No. 6,576,423.

(51) Int. Cl.
*A01N 1/02* (2006.01)
*G01N 33/53* (2006.01)
*C12N 15/85* (2006.01)
*C07K 16/00* (2006.01)

(52) U.S. Cl. ............... 435/7.23; 435/2; 435/7.5; 435/7.92; 435/325; 435/372; 530/387.1; 530/388.1; 530/388.8; 530/391.3

(58) Field of Classification Search .......... 424/130.1, 424/133.1, 141.1, 155.1, 178.1; 435/7.1, 435/7.7, 7.92, 2, 7.23, 7.5, 325, 372; 530/387.1, 530/387.7, 388.8, 391.1, 391.3
See application file for complete search history.

(56) References Cited

U.S. PATENT DOCUMENTS 6,187,536 B1 * 2/2001 Weinberg et al.
6,190,870 B1 * 2/2001 Schmitz et al.
6,673,914 B1 * 1/2004 Hoon

OTHER PUBLICATIONS

Moniaux et al. Journal of Histochemistry and Cytochemistry, 52(2):253-261, 2004.*
Zhang et al. clinical cancer Research, 4(11):2669-2676, 1998.*
Choudhury et al. The Journal of Biological Chemistry. 275(43):33929-33936, Oct. 2000.*
Botti et al. The International Journal of Biological Markers, 12(1):42-43, 1997.*
Botti et al. The International Journal of Biological Markers, 12(4):187-189, 1997.*
Hollingsworth et al. International Journal of Cancer, 57:198-203, 1994.*
Batra et al. Proceedings of the American Association of Cancer Research, 38:421 (#2818), Mar. 1997.*
Lewin B. Genes VI, 1997, CH. 29, pp. 847-848.*
Fu et al. EMBO Journal, 1996, vol. 15, pp. 4392-4401.*
Jang et al. Clinical and Experimental Metastasis, 1997, vol. 15, pp. 469-483.*
Gokman-Polar et al. Cancer Research, 2001, 61:1375-1381.*
Boltz et al. Journal of Cancer Research and Clinical Oncology, 113:291-297, 1987.*
Ashmore et al. Journal of Immunological Methods, 118:209-215, 1989.*
Choudhury, A., et al., "Human MUC4 Mucin cDNA and its Variants in Pancreatic Carcinoma", J. Biochem., 128:233-243 (2000).
Balague, C., et al., "In Situ Hybridization Shows Distinct Patterns of Mucin Gene Expression in Normal, Benign, and Malignant Pancreas Tissues", Gastroenterology, 109: 953-964 (1995).
Trendelenburg G. et al., "Rapid Generation of DNA Probes by Amplification of Tandem Repeats", BioTechniques, vol. 23, p. 242, 244, 246 (1997).
Moniaux, N. et al., "Complete sequence of the human mucin MUC4: a putative cell membrane-associated mucin", Biochem. J., vol. 338, pp. 325-333 (Mar. 1, 1999).
Lazar, J. G., "PCR Primer, A Laboratory Manual", Cold Spring Harbor Laboratory Press, pp. 177-192 (1995).
Stratagene Catalog, p. 39 (1988).
Moniaux, N. et al., "Alternative splicing generates a family of putative secreted and membrane-associated MUC4 mucins", Eur. J. Biochem., vol. 267, pp. 4536-4544 (Jul. 2000).
GeneBank Accession No. AJ010901, *Homo sapiens* MUC4 gene, 3' flanking region, Sep. 23, 2000.
Parker, S.L. et al., "Cancer Statistics, 1996"; CA Cancer J. Clin., 46: 5-27 (1996).
Caldas, C. et al.; "Detection of K-ras Mutations in the Stool of Patients with Pancreatic Adenocarcinoma and Pancreatic Ductal Hyperplasia"; Cancer Research, 54: 3568-3573 (1994).
Tada, M. et al., "Detection of ras Gene Mutations in Pancreatic Juice and Peripheral Blood of Patients with Pancreatic Adenocarcinoma"; Cancer Research, 53: 2472-2474 (1993).

(Continued)

*Primary Examiner*—Larry R. Helms
*Assistant Examiner*—David J. Blanchard
(74) *Attorney, Agent, or Firm*—Dann Dorfman Herrell and Skillman; Kathleen D. Rigaut

(57) ABSTRACT

Methods are provided for the diagnosis of pancreatic cancer.

13 Claims, 2 Drawing Sheets

OTHER PUBLICATIONS

Soeth, E., "Comparative Analysis of Bone Marrow and Venous Blood Isolates from Gastrointestinal Cancer Patients for the Detection of Disseminated Tumor Cells Using Reverse Transcription PCR"; Cancer Research, 57: 3106-3110 (1997).

Burdick, M.D., "Oligosaccharides Expressed on MUC1 Produced by Pancreatic and Colon Tumor Cell Lines"; J. Biol. Chem., 272: 24198-24202 (1997).

Hollingsworth, M.A., "Expression of MUC1, MUC2, MUC3 and MUC4 Mucin MRNAs in Human Pancreatic and Intestinal Tumor Cell Lines"; Int. J. Cancer, 57: 198-203 (1994).

Balagué, C., et al., "Altered Expression of MUC2, MUC4, and MUC5 Mucin Genes in Pancreas Tissues and Cancer Cell Lines"; Gastroenterology, 106: 1054-1061 (1994).

Batra, S.K., et al., "MUC4 Gene Expression in Human Pancreatic Adenocarcinomas"; Proceedings from the American Association of Cancer Research, 38: 421 (1997).

Brugger, W. et al., "Expression of MUC-1 Epitopes on Normal Bone Marrow: Implications for the Detection of Micrometastatic Tumor Cells"; J. Clin. Oncol., 17: 1535-1544 (1999).

Choudhury, A., et al., "Retinoic acid-dependent Transforming Growth Factor-$\beta$2-mediated Induction of *MUC4* Mucin Expression in Human Pancreatic Tumor Cells Follows Retinoic Acid Receptor-$\alpha$ Signaling Pathway"; J. Biol. Chem.; 275: 33929-33936 (2000).

* cited by examiner

MUCIN 4 EXPRESSION AS A MARKER FOR PANCREATIC CANCER

CONTINUING APPLICATION DATA

This application is a divisional of U.S. application Ser. No. 09/733,444, now U.S. Pat. No. 6,576,423, filed Dec. 8, 2000, which is incorporated by reference herein.

GOVERNMENT RIGHT

Pursuant to 35 U.S.C. Section 202(c), it is acknowledged that the United States government has certain rights in the invention described herein, which was made in part with funds from the National Institutes of Health Grant Nos. RO1 CA78590 and P50 CA72712.

FIELD OF THE INVENTION

This invention relates to the fields of molecular biology and oncology. Specifically, the invention provides a molecular marker for use in the diagnosis of pancreatic cancer.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

Pancreatic adenocarcinoma (PA) belongs to a group of neoplasms which exhibit a relatively high level of incidence and poor prognosis (1). In the United States, PA is the fifth leading cause of cancer-related deaths and has the lowest 5-year survival rate of any cancer (2,3). In the year 2000, for example, an estimated 28,600 deaths will be ascribed to this type of cancer and approximately 28,600 new cases will be diagnosed. The molecular basis underlying the pathogenesis of PA remains unknown. As a result, the disease has an extremely poor prognosis and lacks early diagnostic and therapeutic modalities.

PA has a median survival of 9–12 months and an overall 5-year survival rate of 3% for all stages. At the time of diagnosis, over four-fifths of patients with PA have clinically apparent metastatic disease. Among patients whose disease is considered to be resectable, 80% will die of recurrent tumor within 2 years. Surprisingly, these statistics actually represent a decrease in both the operative mortality and overall morbidity associated with PA. Factors which appear to be improving long-term survival include improved pancreatectomy technique, earlier detection, reduced perioperative mortality and decreased blood transfusions.

Early diagnosis of PA is difficult but essential in order to develop improved treatments and a possible cure for this disease. Currently, the ability to detect early lesions for resection remains a diagnostic challenge despite the advances in diagnostic imaging methods like ultrasonography (US), endoscopic ultrasonography (EUS), dualphase spiral computer tomography (CT), magnetic resonance imaging (MRT), endoscopic retrograde cholangiopancreatography (ERCP) and transcutaneous or EUS-guided fine-needle aspiration (FNA). Furthermore, distinguishing PA from benign pancreatic diseases, especially chronic pancreatitis, is difficult because of the similarities in radiological and imaging features and the lack of specific clinical symptoms for PA.

Over the past decade, a remarkable increase in the knowledge of somatic genetic alterations underlying human pancreatic cancer cells has been recorded. Mutations of the K-ras oncogene (~90% of PA cases) and the p53 tumor suppressor gene (50–70%) are the most widely studied genetic tumor markers in pancreatic cancer (4,5). In fact, K-ras mutations have been detected in cytological examinations, from cells present in pancreatic juice and stool samples, as well as in the peripheral blood of patients with pancreatic cancer (6–8). The detection of these mutations have also been associated with chronic pancreatitis (9).

Additionally, there are various highly sensitive PCR-based screening tests for detection of pancreatic cancer cells in blood samples. All of these RT-PCR techniques are based on the detection of genes which are predicted to be specific for pancreatic cancer cells in blood samples (10,11). However, the clinical value, specificity and sensitivity of these molecular tumor markers used in the diagnosis of pancreatic adenocarcinoma differ among the various published studies and are still under evaluation.

The most commonly used clinical tumor markers are serum-based immunoassays for blood group-related antigens and glycoprotein markers, such as CA19-9, CA72-4, CA125, and more recently CA242. However, there are contradictory reports about the specificity and sensitivity of these immunoassays. For example, the specificity of the CA19-9 serum assay for detecting pancreatic cancer ranged from 69% to 93%, and the specificity varied between 46% and 98% (12). Unfortunately, CA19-9 antigen also exhibited elevated serum levels in some benign pancreatic diseases (13).

Further studies have determined that serum marker antigens like CA19-9 are oligosaccharide structures present on mucins. Mucins are heavily glycosylated, high molecular weight proteins that are synthesized and expressed by epithelial cells of the gastrointestinal, respiratory and genitourinary tracts (14–16). The structure of epithelial mucins displays a protein backbone bearing numerous carbohydrate side chains.

To date, 11 different mucins have been described partially or completely (15, 17, 18). These mucins include: MUC1, MUC2, MUC3, MUC4, MUC5AC, MUC5B, MUC6, MUC7, MUC11 and MUC12. Alterations in the expression and structure of these mucins have been reported in different cancers of epithelial origin, such as in pancreatic adenocarcinoma tumors and tumor cell lines, where a dysregulation of MUC1 mucin expression has been described (19–21). Additionally, an aberrant expression of MUC4 in pancreatic cancer cells has also been reported (21–23). The pattern of mucin expression was investigated in pancreatic cancer tissues, pancreatic cancer cell lines and tissue samples of chronic pancreatitis in comparison to normal pancreatic tissue specimens. Pancreatic adenocarcinoma was characterized by an aberrant expression of MUC4 mRNA in 70% of the samples whereas chronic pancreatitis and normal pancreatic tissues were MUC4 negative.

There is some evidence that mucins are also expressed in non-epithelial cells. In recent reports, immune cells, especially T-lymphocytes, were shown to express MUC1 (24–26). The function of MUC1 in immune cells is still under investigation, however, it appears that MUC1 can function as a negative regulator of T cell activation (26).

Despite the improvements of the diagnostic techniques and the knowledge about genetic alterations in mucins, the ability to distinguish between pancreatic cancer and chronic pancreatitis is still a clinical problem. A specific diagnostic test for early detection of pancreatic cancer would greatly aid the clinician in the treatment of this disease.

SUMMARY OF THE INVENTION

In accordance with the present invention, it has been discovered that peripheral blood mononucleocytes (PBMCs) isolated from pancreatic cancer patients are positive for MUC4 while MUC4 expression is not observed in PBMCs isolated from normal patients or from patients suffering from chronic pancreatitis or other types of cancers. Accordingly, methods are provided for assessing PBMCs for the presence of MUC4 as a new tumor marker for pancreatic cancer.

In one embodiment of the invention, a method for detecting MUC4 encoding nucleic acid in a biological sample is provided. The method entails extracting nucleic acids from a sample, contacting the extracted nucleic acid with oligonucleotide primers which specifically hybridize to MUC4 encoding nucleic acids if any are present, and subjecting the hybridized nucleic acid and primers to conditions suitable for polymerase chain reaction amplification. The reaction product is then assessed for amplified MUC4 nucleic acid. Suitable primers for use in the method have a sequence selected from the group consisting of: SEQ ID NO: 3, SEQ ID NO: 4, SEQ ID NO: 5 or SEQ ID NO: 6. Suitable methods for characterizing the reaction product include, without limitation, gel electrophoresis, restriction digest mapping, scintillation counting and filter paper assays.

In a further aspect, kits are provided for performing the method described above. Such a kit comprises at least one pair of primers, a polymerase enzyme suitable for use in polymerase chain reaction, buffers and nucleotides suitable for performing amplification reactions, and optionally an instruction protocol.

In another embodiment of the invention, a method is provided for detecting MUC4 protein in a biological sample. This method entails contacting the biological sample with an antibody or fragment thereof having binding affinity for MUC4, such that MUC4-antibody complexes form if MUC4 is present. The MUC4-antibody complex is then isolated. Such complexes may be assessed using methods which include without limitation, flow cytometric analysis, immunochemical detection or localization and immunoblot analysis. Suitable biological samples include without limitation, pancreatic tissue, PBMCs, and intraductal lesions also referred to as pancreatic intraepithelial neoplasias.

In another aspect of the invention, kits are provided for performing the immunoassay described above. Such a kit comprises an antibody or fragment thereof having binding affinity for MUC4, a detectable label for said antibody and reagents suitable for detecting MUC4-antibody immunocomplexes, if present in the biological sample.

In yet a further aspect of the invention, antibodies immunologically specific for MUC4 are provided. Such antibodies may be monoclonal or polyclonal. Additionally antibody fragments having binding affinity for MUC4 are provided. Such antibody fragments comprise Fab, Fab', F(ab')2, F(v) and Sfv generated recombinantly. The anti-MUC4 antibodies or fragments thereof may be used to advantage in the immunoassays and kits described above.

DETAILED DESCRIPTION OF THE INVENTION

Figure 1:
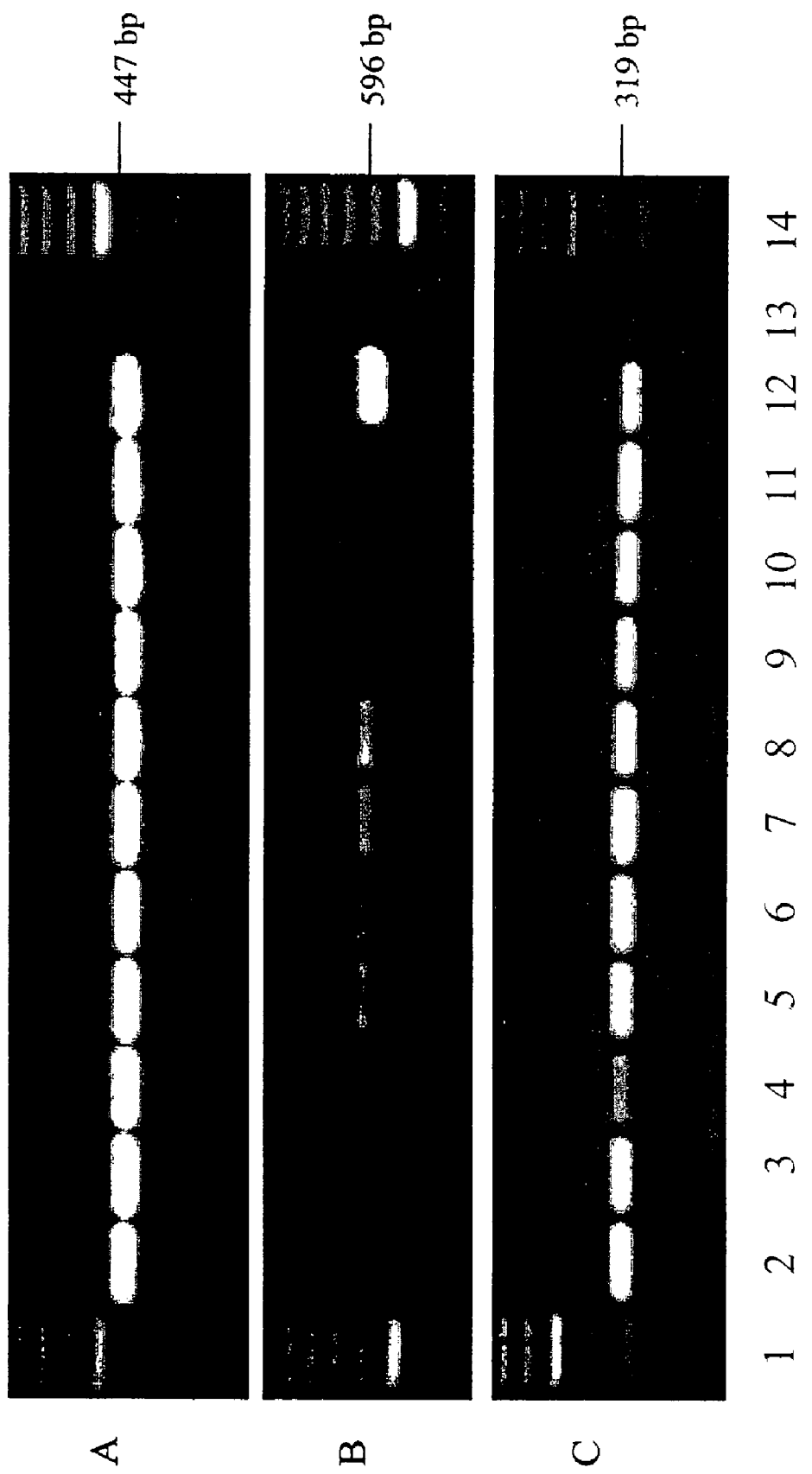
FIG. 1 shows an agarose gel of a polymerase chain reaction assay for MUC1 and MUC4 in selected PBMC samples. Panel A shows the MUC1 PCR product with the expected molecular weight of 447 bp. Panel B provides the MUC4 amplification product in the same PBMC samples. The integrity of the cDNA was tested by amplification of the ribosomal housekeeping gene, RPL13A, which is shown in panel C. Lane 1 shows a PBMC sample from a healthy volunteer, lanes 2 and 3 are from chronic pancreatitis patients, lanes 4, 5, 6 and 7 are from different pancreatic cancer patients, lane 8 is from a patient with colon cancer, lane 9 is from a patient with lung cancer and lane 10 is from a patient with breast cancer. Lane 11 shows the trachea tissue positive control and lane 12 is a negative control. M denotes the molecular size marker.

Pancreatic adenocarcinoma (PA) is the fifth leading cause of cancer-related deaths in the United States. The disease is difficult to detect and has the lowest 5-year survival rate of any cancer (3). This extremely poor prognosis is due to the lack of early diagnostic and therapeutic modalities. In order to increase the survival rate of individuals afflicted with PA, there is an urgent need for specific methods to detect this deadly disease in its earliest stages of development.

Previous studies have examined the expression pattern of mucins in pancreatic cancer (21). Mucins belong to a heterogeneous family of high molecular weight glycoproteins that are widely expressed in epithelial cells. Alterations in the expression and structure of mucins have been reported in different cancers of epithelial origin, such as in pancreatic adenocarcinoma tumors and tumor cell lines (21, unpublished results). Mucins are also expressed in non-epithelial cells. Recent reports demonstrated that MUC1 is expressed in T-lymphocytes (24–26). These results suggest that mucins are potential tumor markers which can be used for diagnosing pancreatic cancer and that mucin expression in non-epithelial cells may provide a preferred target when screening for pancreatic cancer.

In accordance with the present invention, MUC4 expression has been observed in PBMC isolated from the blood of pancreatic cancer patients. Additionally, the expression of MUC4 on T-lymphocytes is highly correlated with the presence of PA. Thus, methods assaying MUC4 expression are provided for diagnosing PA in patients suspected of having pancreatic cancer.

Detection of MUC4 in cells isolated from blood samples may be performed by various methods commonly known to those skilled in the art. In one aspect of the present invention, methods of use are provided for diagnosing pancreatic cancer by screening for MUC4 expression. Such diagnostic methods include without limitation RT-PCR techniques as well as immunospecific methods for the detection of MUC4 associated antigens.

Recent evidence suggests that invasive adenocarcinoma of the pancreas develops through a progression model similar to the adenoma-carcinoma sequence in the colon. Pancreatic adenocarcinoma is believed to develop from histologically identifiable intraductal lesions known as Pancreatic Intraepithelial Neoplasias (PanINs) that undergo a series of architectural, cytological, and genetic changes. Many of the same molecular genetic and protein expression alterations in commonly found in invasive pancreatic adenocarcinoma have been demonstrated in PanIN lesions. MUC4 expression is not detectable at the RNA level in normal pancreas, but is detectable at high levels in invasive pancreatic adenocarcinoma. The pattern of MUC4 expression in PanINs has not previously been described. We also describe herein the pattern of expression of MUC4 in PanINs by studying a series of PanIN lesions immunohistochemically. Accordingly, in yet another aspect of the invention, a method is provided for assessing MUC4 expression in this type of pancreatic interepithelial neoplasia.

I. Definitions

The following definitions are provided to facilitate an understanding of the present invention:

With reference to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eucaryote. An "isolated nucleic acid molecule" may also comprise a cDNA molecule. An isolated nucleic acid molecule inserted into a vector is also sometimes referred to herein as a "recombinant" nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989):

$$T_m = 81.5° C. + 16.6 \text{ Log } [Na+] + 0.41(\% \ G+C) - 0.63$$
$$(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The term "oligonucleotide," as used herein refers to primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15–25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The phrase "solid matrix" as used herein includes, without limitation, filter paper, multiwell dishes, microchips, derivatized magnetic particles and the like.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield an primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The phrase "consisting essentially of" when referring to a particular nucleotide or amino acid means a sequence having the properties of a given SEQ ID No:. For example, when used in reference to an amino acid sequence, the phrase includes the sequence per se and molecular modifications that would not affect the basic and novel characteristics of the sequence.

Polymerase chain reaction (PCR) has been described in U.S. Pat. Nos. 4,683,195, 4,800,195, and 4,965,188, the entire disclosures of which are incorporated by reference herein.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "cell line" is a clone of a primary cell or cell population that is capable of stable growth in vitro for many generations.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2, F(v) and Sfv generated recombinantly.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

II. Preparation of Nucleic Acid Molecules, Probes and Primers

Nucleic acid molecules encoding the oligonucleotides of the invention may be prepared by two general methods: (1) synthesis from appropriate nucleotide triphosphates, or (2) isolation from biological sources. Both methods utilize protocols well known in the art. The availability of nucleotide sequence information, such as the DNA sequence encoding MUC4, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

Specific probes for identifying such sequences as the MUC4 encoding sequence may be between 15 and 40 nucleotides in length. For probes longer than those described above, the additional contiguous nucleotides are provided within the sequence encoding MUC4.

In accordance with the present invention, nucleic acids having the appropriate level of sequence homology with the sequence encoding MUC4 may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42–65° C. in 1×SSC and 1% SDS, changing the solution every 30 minutes.

The nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention, such as selected segments of the sequence encoding MUC4. Also contemplated in the scope of the present invention are oligonucleotide probes which specifically hybridize with the DNA from the sequence encoding MUC4 under high stringency conditions. Primers capable of specifically amplifying the sequence encoding MUC4 are also contemplated to be within the scope of the present invention. As mentioned previously, such oligonucleotides are useful as primers for detecting, isolating and amplifying sequences encoding MUC4.

III. Preparation of MUC4 Antibodies

The present invention also provides antibodies capable of immunospecifically binding to MUC4. Polyclonal antibodies directed toward human MUC4 protein may be prepared according to standard methods. In a preferred embodiment, monoclonal antibodies are prepared, which react immunospecifically with the various epitopes of the MUC4 protein. Monoclonal antibodies have been prepared according to general methods of Kohler and Milstein, following standard protocols. Specifically, various peptides (representing various portions of the MUC4 protein were synthesized and conjugated to the KLH protein as an immunogen and evaluated for their immunogenecity in rabbits. Ten weeks after immunization, rabbit sera demonstrated the presence of bv high titred antibodies (82, 982; 47,338; and 31,108 units) that reacted specifically with MUC4 tandem repeat peptide, (STGDTTPLPVTDTSSV; SEQ ID NO: 27), MUC4 α (ATYRPPQPAWMFGD; SEQ ID NO: 28) and MUC4 β (GARFSYFLNSAEALP; SEQ ID NO: 29) peptides. These polyclonal antibodies showed specific reactivity in immunohistochemistry assays to MUC4 expressing cells.

Mice in three groups were immunized by repeated intraperitoneal injection of the above mentioned peptide antigens. Once an appropriate antibody response was determined by reciprocal 50% endpoint titers in excess of 5,000 vs antigen, the animal was given a final booster injection 3–4 days prior to splenectomy and exsanguination. The lymphocytes were isolated from the spleens and were fused with NS-1 myeloma cells. Those hybridomas producing anti-MUC4 antibodies of interest were selected by screening for specific antibody binding to the MUC4 peptide of interest and a lack of binding to irrelevant control antigens. A panel of monoclonal antibodies immunologically specific for MUC-4 have been obtained in this manner. Polyclonal or monoclonal antibodies that immunospecifically interact with MUC4 protein can be utilized for identifying and purifying MUC4. For example, antibodies may be utilized for affinity separation of proteins with which they immunospecifically interact. Antibodies may also be used to immunoprecipitate proteins from a sample containing a mixture of proteins and other biological molecules. Other uses of anti-MUC4 antibodies are described below.

Purified MUC4 protein, or fragments thereof, may be used to produce polyclonal or monoclonal antibodies which also may serve as sensitive detection reagents for the presence and accumulation of MUC4 protein (or complexes containing MUC4 protein) in mammalian cells. Recombinant techniques enable expression of fusion proteins containing part or all of MUC4 protein. The full length protein or fragments of the protein may be used to advantage to generate an array of monoclonal antibodies specific for various epitopes of MUC4 protein, thereby providing even greater sensitivity for detection of MUC4 protein in cells.

Polyclonal or monoclonal antibodies immunologically specific for MUC4 protein may be used in a variety of assays designed to detect and quantitate the protein. Such assays include, but are not limited to: (1) flow cytometric analysis; (2) immunochemical detection/localization of MUC4 protein in tumor cells or cells in various stages of differentiation; and (3) immunoblot analysis (e.g., dot blot, Western blot) of extracts from various cells. Additionally, anti-MUC4 antibodies can be used for purification of MUC4 protein and any associated subunits (e.g., affinity column purification, immunoprecipitation).

IV. Kits for Performing the Disclosed Methods

Kits are also provided to facilitate the detection of MUC4 in biological samples. Exemplary approaches for detecting MUC4 nucleic acid or polypeptides/proteins include:

a) comparing sequences of nucleic acid in a sample with the MUC4 encoding nucleic acid sequence to determine whether the sample from the patient contains MUC4 sequences; or b) determining the presence, in a sample from a patient, of the polypeptide encoded by the MUC4 gene and, if present, determining whether the polypeptide is full length, and/or is mutated, and/or is expressed at the normal level; or c) using DNA restriction mapping to compare the restriction pattern produced when a restriction enzyme cuts a sample of nucleic acid from the patient with the restriction pattern obtained from normal MUC4 gene or from known mutations thereof; or, d) using a specific binding member capable of binding to a MUC4 nucleic acid sequence (either normal sequence or known mutated sequence), the specific binding member comprising nucleic acid hybridizable with the MUC4 sequence, or substances comprising an antibody domain with specificity for a native or mutated MUC4 nucleic acid sequence or the polypeptide encoded by it, the specific binding member being labeled so that binding of the specific binding member to its binding partner is detectable; or, e) using PCR involving one or more primers based on normal or mutated MUC4 gene sequence to screen for normal or mutant MUC4 gene in a sample from a patient.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples and they do not need to be listed here. Further, the term "specific binding pair" is also applicable where either or both of the specific binding member and the binding partner comprise a part of a large molecule. In embodiments in which the specific binding pair are nucleic acid sequences, they will be of a length to hybridize to each other under conditions of the assay, preferably greater than 10 nucleotides long, more preferably greater than 15 or 20 nucleotides long.

In most embodiments for screening for cancer susceptibility alleles, the MUC4 nucleic acid in the sample will initially be amplified, e.g. using PCR, to increase the amount of the analyte as compared to other sequences present in the sample. This allows the target sequences to be detected with a high degree of sensitivity if they are present in the sample. This initial step may be avoided by using highly sensitive array techniques that are becoming increasingly important in the art.

The identification of the MUC4 gene and its association with cancer paves the way for aspects of the present invention to provide the use of materials and methods, such as are disclosed and discussed above, for establishing the presence or absence in a test sample of a variant form of the gene, in particular an allele or variant specifically associated with cancer, especially pancreatic cancer. This may be for diagnosing a predisposition of an individual to cancer. It may be for diagnosing cancer of a patient with the disease as being associated with the gene.

In still further embodiments, the present invention concerns immunodetection methods for binding, purifying, removing, quantifying or otherwise generally detecting biological components. In general, the immunobinding methods include obtaining a sample suspected of containing a protein or peptide, and contacting the sample with an antibody in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing a MUC4 gene encoded protein or peptide, and contact the sample with an antibody and then detect or quantify the amount of immune complexes formed under the specific conditions.

In terms of antigen detection, the biological sample analyzed may be any sample that is suspected of containing the MUC4 antigen, such as a pancreas or lymph node tissue section or specimen, a homogenized tissue extract, an isolated cell, a cell membrane preparation, separated or purified forms of any of the above protein-containing compositions, or even any biological fluid that comes into contact with pancreatic tissues, including blood and lymphatic fluid.

Contacting the chosen biological sample with an antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e., to bind to, any antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The immunodetection methods of the present invention have evident utility in the diagnosis of pancreatic cancer. Here, a biological or clinical sample suspected of containing either the encoded protein or peptide is used.

In the clinical diagnosis or monitoring of patients with pancreatic cancer, the detection of MUC4, or an increase in the levels of such an antigen, in comparison to the levels in a corresponding biological sample from a normal subject is indicative of a patient with pancreatic cancer. The basis for such diagnostic methods lies, in part, with the finding that the MUC4 nucleic acid identified in the present invention is expressed in pancreatic cancer tissue samples and peripheral blood mononuclear cells(see Example below). By extension, it may be inferred that the MUC4 nucleic acid produces elevated levels of MUC4 protein which may also be used as pancreatic cancer markers.

In one broad aspect, the present invention encompasses kits for use in detecting expression of MUC4 in PBMC. Such a kit may comprise one or more pairs of primers for amplifying nucleic acids corresponding to the MUC4 gene. The kit may also comprise buffers, nucleotide bases, and other compositions to be used in hybridization and/or amplification reactions. Each solution or composition may be contained in a vial or bottle and all vials held in close confinement in a box for commercial sale.

Another embodiment of the present invention encompasses a kit for use in detecting MUC4 antigen in PBMC's. Such a kit may comprise antibodies or antibody fragments immunologically specific for MUC4 and means for assessing the formation of immunocomplexes containing MUC4.

The following examples are provided to illustrate certain embodiments of the invention. They are not intended to limit the invention in any way.

EXAMPLE 1

Detection of MUC4 in Peripheral Blood Mononuclear Cells from Pancreatic Cancer Patients Mucins belong to a heterogeneous family of high molecular weight glycoproteins that are widely expressed in epithelial cells. The expression pattern of mucins has previously been investigated in pancreatic cancer tissues, pancreatic cancer cell lines and tissue samples of chronic pancreatitis in comparison to normal pancreatic tissue specimens to determine whether mucin expression varies in pancreatic cancer (21–23). Data revealed that pancreatic adenocarcinoma was characterized by an aberrant expression of MUC4 mRNA in 70% of the samples, where as chronic pancreatitis and normal pancreatic tissues were MUC4 negative. These results suggest that MUC4 is a candidate marker for pancreatic cancer. Additional evidence indicated that mucins are also expressed in non-epithelial cells, such as T-lymphocytes which were shown to express MUC1 (24–26). Hence, peripheral blood mononuclear cells were examined for MUC4 expression.

The following protocols are provided to facilitate the practice of the present invention.

I. Material and methods

A. Patient Material

In accordance with an IRB study approval, peripheral blood was obtained for isolation of mononuclear cells from 27 patients with pancreatic cancer, 4 with acute pancreatitis, 9 with chronic pancreatitis, 37 with various solid cancers, 10 with haematopoetic malignancies and 10 with non-malignant diseases (See Table 2 and Table 3). Eight healthy volunteers were also included as controls. Patient samples were collected at the University of Nebraska Medical Center, Omaha Nebr. and the Department of Medicine IV, Medical Faculty Mannheim, University of Heidelberg, Germany.

Peripheral blood mononuclear cells (PBMC) were isolated from freshly collected citrated venous blood using FICOLL-PAQUE™ (Accuprep®, Accurate Chemical & Scientific Corp., Westbury, N.Y., USA).

B. Cell Lines

Various established B-cell (Raji, Daudi) and T-cell-derived (Jurkat, MOLT-4, CEM) cell lines were used. The MOLT-4 and CEM cells were kindly provided by Dr. M. A. Hollingsworth (Eppley Cancer Institute, UNMC, Omaha Nebr.). The human hematopoetic cell lines were maintained in RPMI 1640 (Life Technologies, Inc.) supplemented with 10% fetal calf serum.

Human pancreatic cancer cell lines CAPAN-2, HPAF, MiaPaCa and Panc-1 cells (all from ATCC) were cultivated in DMEM with GlutaMAX I supplemented with 10% heat-inactivated fetal calf serum, 2 mM glutamine, and antibiotics (100 units/ml penicillin, 100 µg/ml streptomycin-G, all from Life Technologies, Inc.).

C. Stimulation and Culture Conditions

Freshly prepared PBMC ($10 \times 10^6$ cells) from healthy volunteers were stimulated with PHA (10 µg/ml) and LPS (20 µg/ml, all from Sigma) for 12 and 24 hours. To study the effect of different cytokines and growth factors on the MUC4 mRNA expression, 10 million PBMC were incubated with TGF-$\beta$1 (10; 20 and 200 pg/ml), TGF-$\beta$2 (10; 20 and 200 pg/ml) (all from R&D systems, Minneapolis, Minn.), retinoic acid (RA) (100 nM; 1 µM) (Sigma), GM-CSF (100 U/ml) (Immunex Corp. Seattle, Wash.), IL-1$\beta$ (10 ng/ml), IL-6 (10 ng/ml), IL-9 (50 ng/ml), IFN$\gamma$ (10 and 20 ng/ml), TNF$\alpha$ (10 and 50 ng/ml) or with IFN$\gamma$ (10 and 20 ng/ml) in combination with TNF$\alpha$ (10 and 50 ng/ml) (all from PeproTech Inc., Rocky Hill, N.J.) for 24 and 48 hours under serum free conditions.

PBMC ($10 \times 10^6$ cells) were cultured in the presence of serums as well serum depleted with or without pancreatic cancer cell-derived supernatant. The pancreatic cancer cell supernatant were produced seeding CAPAN-1, HPAF, MiaPaCa or PANC-1 cells ($10 \times 10^6$ cells) for 72 hours in a 75-cm$^2$ flask in the presence of culture medium without serum. The supernatant was collected, filtered to remove all cells and debris, and then added to the lymphocytes at a final dilution of 1:1 with RPMI-1654 medium.

For preparation of concentrated protein the supernatants were collected after incubation for two days, filter sterilized and concentrated using a centrifugation concentrator device (Millipore Corp., Bedford, Mass.) according to the manufacturer's recommendations.

Cell membrane preparations from Capan1, HPAF, MiaPaCa and Panc1 cells were performed as described recently (27). In brief, cells were grown in 175 cm$^2$ culture flasks. For membrane preparation, cells were rinsed once with chilled STE buffer (100 mM NaCl; 10 mM Tris/HCl pH 7.4) and removed from the tissue culture flasks into STE buffer with a cell scraper. Cells were centrifuged at 1000 g for 5 minutes and resuspended in ice-cold hypotonic lysis buffer (10 mM Tris/HCl pH 7.4; 0.2 mM MgCl containing protease inhibitors 1 mM PMSF, aprotinin,leupeptin and DTT).

In addition, freshly prepared PBMC from healthy volunteers were co-cultured with pancreatic cancer cells. Non-contact co-cultivations of the human pancreatic tumor cell lines and PBMC were carried out using 6-well plates and cell-culture inserts (BD, Franklin Lakes, N.Y.) allowing a bidirectional diffusion of molecules. First $5 \times 10^5$ pancreatic cells were seeded onto transwell inserts and were co-cultivated with freshly prepared PBMC ($1 \times 10^6$ cells/well) seeded in 6-well tissue culture plates using RPMI-1654 medium. After 24 hours, cells were collected and RNA was prepared for subsequent analysis as described below. For controls, PBMC was co-cultivated with PBMC, and pancreatic cancer cells were co-cultivated with pancreatic cancer cells.

D. Flow Cytometry and Cell Sorting

For cell sorting, PBMC were washed twice with PBS and were double color stained by incubation with FITC-conjugated anti-CD3 mAb and PE-conjugated anti-CD19 mAb or with anti-CD4-FITC labeled mAb and anti-CD8-PE conjugated mAb (Becton Dickinson, San Jose, Calif.) for 30 minutes on ice and were washed twice with PBS. Sorted cells that were CD3 and CD19-positive or CD4 and CD8-positive were collected in separate tubes prefilled with PBS. Flow cytometric analysis after sorting was performed with fluorescence-activated cell sorter (FACS) SCAN (Becton Dickinson; San Jose, Calif.) using the standard software LYSIS II. FACS analyses of the sorted cell population showed purity of the separated fractions of $\geq 95\%$ in all experiments.

E. RNA Preparation

The single step RNA isolation method was used for RNA preparation as previously described (28,29). In brief, cells were homogenized in a denaturing solution containing 4 M guanidine thiocyanate. The homogenate was mixed sequentially with 2 M sodium acetate (pH 4), phenol and chloroform/isoamyl alcohol. After centrifugation, the RNA in the upper aqueous phase was precipitated with an equal volume of isopropanol over night, washed with 75% ethanol and dried under vacuum. The RNA pellet was then resuspended in diethyl pyrocarbonate (DEPC)-treated water, and the final RNA concentration was determined spectrophotometrically by measuring the absorbance at 260 nm and 280 nm (DU 640B, Beckman Coulter, Fullstone Calif.).

F. Reverse Transcription-PCR Analysis

Total RNA (1 µg) was reverse transcribed using SuperScript II RNase Reverse Transcriptase (Life Technologies, Inc.). Samples were subjected to PCR amplification in a final reaction volume of 50 µl containing 5 µl of 10×buffer (Life Technologies, Inc.), 1.5 µl of 50 mM MgCl$_2$ (Life Technologies, Inc.), 5 µl of 10 mM dNTPs, 10 pmoles of each primer, 2.5 µl of DMSO (Sigma) and 2.5 units of Taq DNA Polymerase (Life Technologies, Inc.). To confirm the presence and integrity of the cDNA template, the ribosomal housekeeping gene, RPL13A, was amplified for each sample using primers Rb1 (5'CATCGTGGCTAAACAGGTACTG 3; SEQ ID NO: 1) and Rb2 (5'GCACGACCT-TGAGGGCAGCC 3'; SEQ ID NO: 2). Conditions were as follows: an initial denaturation step for 4 minutes at 94° C. then 45 seconds at 94° C., 45 seconds at 60° C., and 45 seconds at 72° C. for 30 cycles, followed by an elongation step for 15 minutes at 72° C.

MUC1 RT-PCR was performed using primers that were published previously (30). The parameters were as follows: The first denaturation step was at 94° C. for 4 minutes, followed by 35 cycles of denaturation at 94° C. for 30 seconds; Primer annealing occurred at 58° C. for 45 seconds, and elongation at 72° C. for 45 seconds. The final elongation step was conducted at 72° C. for 15 minutes.

MUC4 amplification was performed using the following primers: primer A (5'CGCGGTGGTGGAGGCGTTCTT 3'; SEQ ID NO: 3) and primer B 5'GAAGAATCCTGACAGC-CTTCA 3'; SEQ ID NO: 4). Forty cycles of the above-described PCR conditions were then repeated for MUC4 amplification, followed by 30 more cycles of amplicfication using nested MUC4 RT-PCR using primer C (5'ACGTTC-CACGGAGGAGTGAGG 3'; SEQ ID NO: 5) and primer D (5'CCTTCCCTTTTCCAGTCTCCC 3'; SEQ ID NO: 6) under the same conditions, exept that the annealing temperature was 60° C.

For the nested RT-PCR amplification, chymotrypsinogen and cytokeratin 20 (CK-20) conditions and primers were used as described previously (10,11). The characteristics of all the primers used in this study are provided in Table I below. The numbers after the sequences are SEQ ID NOS.

TABLE 1

Primer Sequences Used for RT-PCR

| Gene | Accession number | Primer sequence (5' à 3') forward/reverse | Localization (NT) | Product size (bp) |
|---|---|---|---|---|
| MUC1 | J05582 | GAACTACGGGCAGCTGGACATC (SEQ ID NO: 7) | 3640–3661 | 447 |
|  |  | GCTCTCTGGGCCAGTCCTCCT (SEQ ID NO: 8) | 4086–4065 |  |
| MUC2 | L21998 | CTGCACCAAGACCGTCCTCATG (SEQ ID NO: 9) | 15291–15312 | 401 |
|  |  | GCAAGGACTGAACAAAGACTCAGAC (SEQ ID NO: 10) | 15688–15667 |  |
| MUC3 | AF007194 | AGTCCACGTTGACCACCACTGC (SEQ ID NO: 11) | 2526–2547 | 522 |
|  |  | TGTTCACATCCTGGCTGGCG (SEQ ID NO: 12) | 2931–2912 |  |
| MUC4 | AJ010901 | CGCGGTGGTGGAGGCGTTCTT (SEQ ID NO: 3) | 2994–3014 | 596 |
|  |  | GAAGAATCCTGACAGCCTTCA (SEQ ID NO: 4) | 3589–3569 |  |
| MUC4 nested | AJ010901 | ACGTTCCACGGAGGAGTGAGG (SEQ ID NO: 5) | 3020–3040 | 545 |
|  |  | CCTTCCCTTTTCCAGTCTCCC (SEQ ID NO: 6) | 3545–3565 |  |
| MUC5AC | JAJ001402 | TGATCATCCAGCAGCAGGGCT (SEQ ID NO: 13) | 2897–2917 | 409 |
|  |  | CCGAGCTCAGAGGACATATGGG (SEQ ID NO: 14) | 3305–3284 |  |
| MUC5B | Y09788 | CTGCGAGACCGAGGTCAACATC (SEQ ID NO: 15) | 9057–9078 | 415 |
|  |  | TGGGCAGCAGGAGCACGGAG (SEQ ID NO: 16) | 10127–10108 |  |
| MUC6 | U97698 | GCATGGCGAACGTGACGGTAA (SEQ ID NO: 17) | 1034–1054 | 421 |
|  |  | TAGTCTGAGCCCCTGCTTGGCA (SEQ ID NO: 18) | 1454–1433 |  |
| MUC7 | L13283 | CCACACCTAATTCTTCCCCAACTAC (SEQ ID NO: 19) | 1022–1046 | 407 |
|  |  | CTGGCTTGTGGGATAGAGGCATT (SEQ ID NO: 20) | 1428–1406 |  |
| CHYM | M2400.1 | CTCATCAGCGAGGACTGG (SEQ ID NO: 21) | 206–223 | 434 |
|  |  | CAGGGCTGCCTGCTGCAG (SEQ ID NO: 22) | 533–550 |  |
| CHYM nested | M2400.1 | CCCACTGCGGGGTCAGGA (SEQ ID NO: 23) | 237–254 | 287 |
|  |  | GGGTCTTGTTGGCGTTGTA (SEQ ID NO: 24) | 506–524 |  |
| RPL13A (Rb23) | NM012423 | CATCGTGGCTAAACAGGTACTG (SEQ ID NO: 25) | 80–399 | 319 |
|  |  | GCACGACCTTGAGGGCAGCC (SEQ ID NO: 26) |  |  |

To verify that the amplified products were from mRNA and not genomic DNA contamination, negative controls were performed by omitting the RT. In the absence of RT, no PCR products were detected. A total of 20 μl of each PCR product were electrophoretically resolved on 1% agarose gel stained with ethidium bromide. Following exposure to UV light, the density of DNA bands was determined using the GelExpert software system (Nucleotech Corp., Santa Mateo, Calif.).

To confirm the identity of the PCR products the amplified DNA fragments were ligated to pCR 2.1 vector using the TA cloning kit and then transformed into *E. coli* (all from Invitrogen, Carlsbad, Calif.) as recommended by the manufacturer. Then the amplified DNA fragments were sequenced using vector primers.

G. Immunohistochemical Staining

Immunohistochemical analysis was performed using a polyclonal anti-human MUC4 rabbit serum as described previously (31). Tissue sections were stained with polyclonal anti-human MUC4 rabbit serum or with pre-immune rabbit serum serving as negative control.

II. Results

In order to determine whether MUC4 is a molecular marker for pancreatic cancer, the expression of mucin mRNA was examined in samples of peripheral blood mononuclear cells (PBMC).

A. Mucin Expression in PBMC of Healthy Individuals

Mucin expression was first analyzed in PBMC cells from healthy individuals using RT-PCR technique. Only MUC1 mRNA was found in these PBMC cell samples. Lane 1 of FIG. 1 shows MUC1 mRNA expression from a healthy individual. In contrast, MUC4 mRNA was not detected in any of the healthy individual samples. However, MUC4 mRNA from trachea tissue, a positive control, was detected (FIG. 1, lane 11).

B. Mucin Expression in PBMC of Patients with Pancreatitis and Pancreatic Cancer

To obtain a comparative picture of mucin RNA expression between healthy individuals and those with cancer, the expression pattern of mucins was examined in various well-characterized malignant hematopoietic cell lines with B- or T-cell origin.

MUC1 mRNA was detected in all investigated cell lines. Surprisingly, investigation of PBMC samples from pancreatic cancer patients revealed that in 18/27 (67%) of pancreatic cases, MUC4 mRNA was present (See Table 2).

To confirm, that MUC4 RNA detection was not the result of contamination with circulating pancreatic cancer cells, two recently published, highly sensitive nested RT-PCR-based detection assays were used for detection of micrometastasis (10, 11). Interestingly, in only two of the PBMC samples from pancreatic cancer patients (patients 6 and 19) was CK-20, a marker for epithelial cells, detected in the sample. Patient sample 6 was also positive for MUC4 mRNA, whereas patient 19 was MUC4 mRNA negative (Table 2). Amplification of pancreas-specific chymotrypsinogen was also found in both PBMC samples from patients 6 and 19.

TABLE 2

MUC4 Expression Pattern in PBMC From Patients with Pancreatic Adenocarcinoma

| Patient number | Sex | Age | AJCC Stage | MUC4 mRNA expression | CK-20 mRNA | Chymotrypsinogen mRNA |
|---|---|---|---|---|---|---|
| 1 | M | 69 | IVB | + | − | − |
| 2 | F | 52 | IVB | + | − | − |
| 3 | M | 52 | III | + | − | − |
| 4 | M | 49 | IVB | − | − | − |
| 5 | M | 41 | III | + | − | − |
| 6 | M | 72 | IVB | + | + | + |
| 7 | F | 54 | III | + | − | − |
| 8 | M | 66 | II | + | − | − |
| 9 | M | 63 | IV | + | − | − |
| 10 | F | 65 | IVA | + | − | − |
| 11 | F | 66 | IVA | + | − | − |
| 12 | M | 66 | IV | + | − | − |
| 13 | M | 77 | III | + | − | − |
| 14 | F | 62 | IVB | − | − | − |
| 15 | M | 78 | IVB | + | − | − |
| 16 | M | 75 | II | − | − | − |
| 17 | M | 48 | II | + | − | − |
| 18 | F | 81 | II | − | − | − |
| 19 | F | 54 | IVB | − | − | + |
| 20 | M | 78 | IV | − | − | − |
| 21 | M | 63 | III | − | − | − |
| 22 | M | 62 | | − | − | − |
| 23 | F | 73 | IVB | + | − | − |
| 24 | F | 69 | | + | − | − |
| 25 | M | 55 | | + | − | − |
| 26 | F | 45 | IV | − | − | − |
| 27 | M | 52 | | + | − | − |

C. Mucin Expression in PBMC of Patients with other Malignancies or Non-Malignant Diseases A group of patients with various types of epithelial and haematopoetic malignancies was also examined for mucin expression (See Table 3). MUC1 mRNA expression was dectected in all of the malignancy and non-malignant disease samples tested. However, none of the samples showed detectable levels of MUC4 mRNA. In addition, MUC4 mRNA was not amplified in PBMC from patients with benign pancreatic diseases including acute and chronic pancreatitis. These results indicate that the expression of MUC4 mRNA in PBMC samples was 100% specific for pancreatic cancer. Thus, MUC4 mRNA expression in PBMC can be used as a specific tumor marker for pancreatic cancer.

TABLE 3

Expression of MUC1 and MUC4 in PBMC from Patients with Malignant and Chronic Diseases

| Diagnosis | MUC1 | MUC4 |
|---|---|---|
| Other solid malignancies | 37/37 | 0/37 |
| Colon/Rectal | 12/12 | 0/12 |
| Esophagial | 6/6 | 0/6 |
| Gastric | 2/2 | 0/2 |
| Ampullary | 1/1 | 0/1 |
| Lung | 5/5 | 0/5 |
| Head/neck | 2/2 | 0/2 |
| Breast | 4/4 | 0/4 |
| Lanryngeal | 2/2 | 0/2 |
| Tongue | 1/1 | 0/1 |
| Parotis (basal cell) | 1/1 | 0/1 |
| Thyroid | 1/1 | 0/1 |
| Hematopoietic malignancies | 10/10 | 0/10 |
| CLL (B-cell type) | 4/4 | 0/4 |
| CML | 1/1 | 0/1 |
| Multiples Myeloma | 5/5 | 0/5 |
| Other diseases* | 10/10 | 0/10 |

Other diseases include: mucinous ductal actasy (n = 1), asthma (n = 7), billiary obstruction unknown origins (n = 1), mucinous ductal actasia (n = 1)

D. Detection of MUC4 mRNA in T-Lymphocytes

Figure 2:
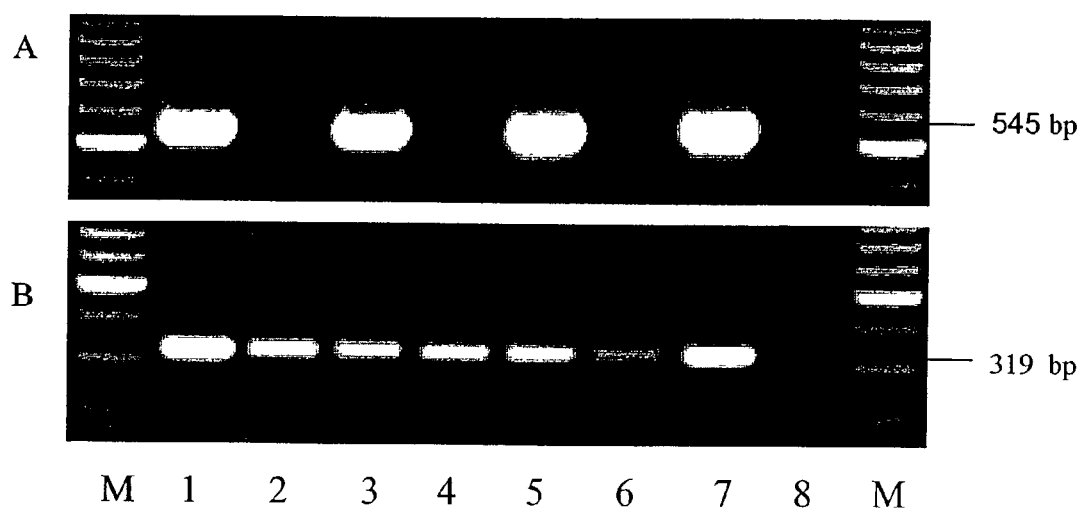
FIG. 2 shows the agarose gel of a nested MUC4 RT-PCR product in sorted T- and B-lymphocytes of pancreatic cancer patients. The PBMCs of three MUC4 positive pancreatic cancer patients were sorted for CD3 (T-cells) and CD19 (B-cells). Panel A shows the 545 bp amplification of the nested MUC4 RT-PCR was present in all of the CD3 positive samples, but absent in the CD19-positive subpopulations. The amplification product of the ribosomal housekeeping gene, RPL13A, is shown in panel B. Lanes 1, 3 and 5 show the CD3-cells from pancreatic cancer patients 8, 9 and 12. Lanes 2, 4 and 6 demonstrate the CD19-cells from the same patients. Lane 7 shows the trachea tissue positive control and lane 8 is the negative control. M demonstrates the molecular size marker.

To determine which cell subtype expressed MUC4 mRNA, PBMC samples from three MUC4 positive pancreatic cancer patients were sorted by flow cytometric cell sorting. This allowed for separation of CD3+ T-lymphocytes and CD19+ B-Lymphocyte subpopulations. The T-lymphocytes from one patient showed a weak amplification in the first RT-PCR. The nested PCR showed MUC4 mRNA amplification in all investigated CD3+ T-lymphocytes, whereas the CD19+ B-lymphocytes were negative (See FIG. 2). This data indicates a T-lymphocyte-based expression of MUC4 transcript.

E. MUC4 mRNA Expression Induced by MUC4 Postive Pancreatic Cancer Cells

The present inventors previously demonstrated that MUC4 mRNA expression in pancreatic cancer cells is induced by serum-related and micro-environmental-based factors (31). In an effort to understand the possible regulation mechanisms for the induction of MUC4 mRNA in lymphocytes specific in pancreatic cancer, a panel of in vitro assays were performed whereby PBMC and supernatant from healthy volunteers was incubated with either: (1) the concentrated supernatant proteins or the purified cell membrane fraction of strong MUC4 positive pancreatic cancer cell lines, Capan1 or HPAF, (2) Panc1 cells or (3) the MUC4 negative cell line, MiaPaCa. These experiments showed that only the cell-contact free co-cultivation with Capan1, HPAF and Panc1 could induce a weak MUC4 mRNA expression in the PBMC, whereas MiPaCa had no effect (data not shown). Contaminations of the PBMC with pancreatic cancer cells were excluded by using the above-described CK-20 and chymotrypsinogen nested RT-PCR assays (data not shown).

Flow cytometric sorting was also performed using the co-cultured PBMC to sort CD4+ T-helper cells and CD8+ cytotoxic T-cells. Cell sorting revealed a faint MUC4 mRNA amplification in the CD8+ cytotoxic T-cell subpopulation.

This data stongly suggests that secreted factors related to the pancreatic cancer cells are involved in MUC4 induction in T-cells. Previously, treatment with retinoic acid and TGF-β2, which is produced and secreted by pancreatic cancer cell lines, resulted in MUC4 expression (31). But neither incubation with retinoic acid and TGF-β2 nor the activation of T-cells and B-cells with PHA and LPS or incubation with various other cytokines induced MUC4 mRNA expression in PBMC samples.

EXAMPLE 2

MUC4 Expression Increases Progressively in Pancreatic Intraepithelial Neoplasia

Recent evidence suggests that there is a neoplastic progression in the pancreas that is very similar to the adenoma-carcinoma sequence in the colon (4–7). In this process, non-invasive neoplastic mucinous epithelium with cytological and architectural atypia replaces the normal nonmucinous, cuboidal epithelium of the pancreatic ducts and ductules. Such lesions, known as Pancreatic Intraepithelial Neoplasias (PanINs), have recently been definitively classified (8). PanINs are believed to progress from flat to papillary lesions without atypia, to papillary lesions with atypia, to lesions with severe architectural and cytologic atypia (PanIN-1A to PanIN-1B to PanIN-2 to PanIN-3) (6–11). Some atypical intraductal lesions eventually progress to infiltrating adenocarcinoma (7). Not surprisingly, many of the alterations in cancer-associated genes that occur in invasive pancreatic adenocarcinoma have also been demonstrated in a variety of PanINs by both direct genetic analysis and immunohistochemical analysis of expressed proteins (12–21). Characterization of the patterns of these alterations in a spectrum of morphologically well-characterized PanINs has helped to establish the temporal occurrence of these genetic alterations in the pancreatic cancer progression model. The present example describes the results of analysis of MUC4 expression in a large series of PanINs, adjacent non-neoplastic pancreas, and invasive pancreatic adenocarcinomas by immunohistochemistry.

The following materials and methods are provided to facilitate the practice of Example II.

Case Selection:

Pancreaticoduodenectomy specimens (Whipple resection specimens) from 40 patients were studied. Thirty-eight resections were performed for infiltrating adenocarcinoma, and two resections were performed for chronic pancreatitis. Fifty-six formalin-fixed paraffin-embedded tissue blocks were chosen because they contained a well-defined PanIN lesion on their corresponding original hematoxylin and eosin stained section. When the blocks were recut for this study, 18 of these 56 tissue blocks did not contain the PanIN lesion, presumably because the lesion was small and had been completely utilized in previous sections. Nonetheless, these 18 blocks contained normal pancreatic ducts, and 7 contained invasive pancreatic carcinoma. Also, two of the blocks contained ducts with reactive epithelial changes arising in the setting of chronic pancreatitis.

Immunohistochemistry:

Unstained 4 micron sections were treated with a 1:3000 dilution of a mouse monoclonal antibody (clone 8G7) to MUC4 using previously described methodology (20). Briefly, each slide was deparaffinized by routine techniques, treated with sodium citrate buffer (diluted to 1×HIER buffer from 10×HIER buffer; Ventana-Bio Tek Solutions, Tuscon, Ariz.), and steamed for 20 min at 80 degrees Celsius. After cooling for 5 minutes, the slides were labeled with the antibody using the Bio Tek-Mate 1000 automated stainer (Ventana-BioTek Solutions). The bonding of the anti-MUC4 antibody was detected by adding biotinylated secondary antibodies, avidin-biotin complex, and 3,3'-diaminobenzidine. Sections were counterstained with hematoxylin. For negative controls, the primary antibody was replaced with normal saline.

Grading of Duct Lesions:

Once labeled immunohistochemically, duct lesions were graded by four of the authors of this study (MJS, PA, REW, and RHH) at a multi-observer microscope, and a consensus grade was deduced. Criteria established at the National Cancer Institute-sponsored Pancreas Cancer Think Tank in September, 1999, in Park City, Utah were used to classify each lesion (8).

Immunohistochemical Interpretation:

The lesions were evaluated using immunohistochemical labeling. The labeling of each lesion was scored as "positive," "focal positive," or "negative" (20). Positive labeling was defined as strong expression of MUC4 in the cytoplasm of the majority (>50%) of cells. Focal labeling (1–50% of cells) was also classified as positive for data analysis. Lesions were deemed negative only when there was no detectable expression of MUC4. Sections from normal gastric mucosa, where MUC4 is normally expressed, served as positive control.

Results

A total of 71 PanIN lesions were labeled immunohistochemically with the MUC4 antibody. Twenty-five lesions were graded as PanIN-1A, 5 as PanIN-1B, 28 as PanIN-2, and 13 as PanIN-3. In addition, 28 invasive adenocarcinomas were also evaluated. The results are summarized in Table 1. PanIN-1A and PanIN-1B lesions were combined into one group and referred to as PanIN-1 lesions for the purposes of data analysis because of the known similarities in their genetic alterations (8). Seventeen percent of PanIN-1 lesions, thirty-six percent of PanIN-2 lesions, eighty-five percent of PanIN-3 lesions, and eighty-nine percent of invasive cancers labeled with the MUC4 antibody. A significant percentage of the positive cases showed focal labeling; less than half of the duct cells labeled in 40% of the positive PanIN-1 lesions, 70% of the PanIN-2 lesions, 27% of the PanIN-3 lesions, and 32% of the invasive carcinomas.

None of the normal pancreatic ducts, acini, islets, or surrounding nonepithelial elements (lymphocytes or stroma) labeled for MUC4. However, in addition to the PanINs and invasive carcinomas, a number of non-neoplastic duct lesions showed expression of the MUC4 protein. Four of seven atrophic duct profiles in five sections bearing inspissated secretions labeled for MUC4. Thirteen of twenty-two duct profiles with reactive epithelial changes arising in the setting of marked inflammation labeled for MUC4. In these chronic pancreatitis sections, labeling of the reactive ducts was patchy; all 13 labeled focally (<50% of cells), and of these 9 demonstrated only rare MUC4 positive cells. Two other sections contained ducts with squamous metaplasia that labeled for MUC4. In addition, focal MUC4 expression was seen in an accessory pancreatic duct entering the duodenum and in peribiliary glands.

TABLE 4

Labeling of pancreatic ductal lesions for MUC4

| Type of lesion | Total number | Number positive (Number focal positive) | Percent positive |
|---|---|---|---|
| PanIN1 | 30 | 5 (2) | 17 |
| PanIN2 | 28 | 10 (7) | 36 |
| PanIN3 | 13 | 11 (3) | 85 |
| Invasive carcinoma | 28 | 25 (8) | 89 |

We have shown that immunohistochemistry is an effective and convenient method for determining MUC4 expression in a large number of pancreatic duct lesions. We have also shown MUC4 glycoprotein expression increased with increasing grade in PanIN. Accordingly, methods for assessing MUC4 expression provide the clinician with an additional screening test for invasive pancreatic carcinoma.

REFERENCES FOR EXAMPLE I

1. Warshaw A L, Fernandez-del C C. Pancreatic carcinoma. N Engl J Med 1992; 326:455–465.
2. DiMagno E P, Reber H A, Tempero M A. AGA technical review on the epidemiology, diagnosis, and treatment of pancreatic ductal adenocarcinoma. American Gastroenterological Association. Gastroenterology 1999; 117:1464–1484.
3. Parker S L, Tong T, Bolden S, Wingo P A. Cancer statistics, 1996. CA Cancer J Clin 1996; 46:5–27.
4. Kondo H, Sugano K, Fukayama N, Kyogoku A, Nose H, Shimada K, et al. Detection of point mutations in the K-ras oncogene at codon 12 in pure pancreatic juice for diagnosis of pancreatic carcinoma. Cancer 1994; 73:1589–1594.
5. Redston M S, Caldas C, Seymour A B, Hruban R H, da Costa L, Yeo C J, et al. p53 mutations in pancreatic carcinoma and evidence of common involvement of homocopolymer tracts in DNA microdeletions. Cancer Res 1994; 54:3025–3033.
6. Caldas C, Hahn S A, Hruban R H, Redston M S, Yeo C J, Kern S E. Detection of K-ras mutations in the stool of patients with pancreatic adenocarcinoma and pancreatic ductal hyperplasia. Cancer Res 1994; 54:3568–3573.
7. Shibata D, Almoguera C, Forrester K, Dunitz J, Martin S E, Cosgrove M M, et al. Detection of c-K-ras mutations in fine needle aspirates from human pancreatic adenocarcinomas. Cancer Res 1990; 50:1279–1283.
8. Tada M, Omata M, Kawai S, Saisho H, Ohto M, Saiki R K, et al. Detection of ras gene mutations in pancreatic juice and peripheral blood of patients with pancreatic adenocarcinoma. Cancer Res 1993; 53:2472–2474.
9. Lohr M, Maisonneuve P, Lowenfels A B. K-Ras mutations and benign pancreatic disease. Int J Pancreatol 2000; 27:93–103.
10. Kuroki T, Tomioka T, Tajima Y, Inoue K, Ikematsu Y, Ichinose K, et al. Detection of the pancreas-specific gene in the peripheral blood of patients with pancreatic carcinoma. Br J Cancer 1999; 81:350–353.
11. Soeth E, Vogel I, Roder C, Juhl H, Marxsen J, Kruger U, et al. Comparative analysis of bone marrow and venous blood isolates from gastrointestinal cancer patients for the detection of disseminated tumor cells using reverse transcription PCR. Cancer Res 1997; 57:3106–3110.
12. Eskelinen M, Haglund U. Developments in serologic detection of human pancreatic adenocarcinoma. Scand J Gastroenterol 1999; 34:833–844.
13. Slesak B, Harlozinska-Szmyrka A, Knast W, Sedlaczek P, Van Dalen A, Einarsson R. Tissue polypeptide specific antigen (TPS), a marker for differentiation between pancreatic carcinoma and chronic pancreatitis. A comparative study with CA 19-9. Cancer 2000; 89:83–88.
14. Kim Y S, Gum J R J, Crawley S C, Deng G, Ho J J. Mucin gene and antigen expression in biliopancreatic carcinogenesis. Ann Oncol 1999; 10 Suppl 4:51–55.
15. Gendler S J, Spicer A P. Epithelial mucin genes. Annu Rev Physiol 1995; 57:607–634.
16. Lesuffleur T, Zweibaum A, Real F X. Mucins in normal and neoplastic human gastrointestinal tissues. Crit Rev Oncol Hematol 1994; 17:153–180.
17. Pratt W S, Crawley S, Hicks J, Ho J, Nash M, Kim Y S, et al. Multiple transcripts of MUC3: evidence for two genes, MUC3A and MUC3B [In Process Citation]. Biochem Biophys Res Commun 2000; 275:916–923.
18. Williams S J, McGuckin M A, Gotley D C, Eyre H J, Sutherland G R, Antalis T M. Two novel mucin genes down-regulated in colorectal cancer identified by differential display. Cancer Res 1999; 59:4083–4089.
19. Burdick M D, Harris A, Reid C J, Iwamura T, Hollingsworth M A. Oligosaccharides expressed on MUC1 produced by pancreatic and colon tumor cell lines. J Biol Chem 1997; 272:24198–24202.
20. Tashiro Y, Yonezawa S, Kim Y S, Sato E. Immunohistochemical study of mucin carbohydrates and core proteins in human ovarian tumors. Hum Pathol 1994; 25:364–372.
21. Hollingsworth M A, Strawhecker J M, Caffrey T C, Mack D R. Expression of MUC1, MUC2, MUC3 and MUC4 mucin mRNAs in human pancreatic and intestinal tumor cell lines. Tnt J Cancer 1994; 57:198–203.
22. Balague C, Gambus G, Carrato C, Porchet N, Aubert J P, Kim Y S, et al. Altered expression of MUC2, MUC4, and MUC5 mucin genes in pancreas tissues and cancer cell lines. Gastroenterology 1994; 106:1054–1061.
23. Batra S K, Bhattacharyya S N, Kaufman B, Hollingsworth M A. MUC4 gene expression in human pancreatic adenocarcinomas. Proceedings from the American Association of Cancer Research 1997; 38:421
24. Agrawal B, Krantz M J, Parker J, Longenecker B M. Expression of MUC1 mucin on activated human T cells: implications for a role of MUC1 in normal immune regulation. Cancer Res 1998; 58:4079–4081.
25. Brugger W, Buhring H J, Grunebach F, Vogel W, Kaul S, Muller R, et al. Expression of MUC-1 epitopes on normal bone marrow: implications for the detection of micrometastatic tumor cells. J Clin Oncol 1999; 17:1535–1544.
26. Chang J F, Zhao H L, Phillips J, Greenburg G. The epithelial mucin, MUC1, is expressed on resting T lymphocytes and can function as a negative regulator of T cell activation. Cell Immunol 2000; 201:83–88.
27. Schlondorff J, Becherer J D, Blobel C P. Intracellular maturation and localization of the tumour necrosis factor alpha convertase (TACE). Biochem J 2000; 347 Pt 1:131–138.
28. Chomczynski P, Sacchi N. Single-step method of RNA isolation by acid guanidinium thiocyanate-phenol-chloroform extraction. Anal Biochem 1987; 162:156–159.

29. Sparmann G, Jaschke A, Loehr M, Liebe S, Emmrich J. Tissue homogenization as a key step in extracting RNA from human and rat pancreatic tissue. Biotechniques 1997; 22:408–10, 412.
30. Lan M S, Batra S K, Qi W N, Metzgar R S, Hollingsworth M A. Cloning and sequencing of a human pancreatic tumor mucin cDNA. J Biol Chem 1990; 265: 15294–15299.
31. Choudhury A, Singh R K, Moniaux N, El-Metwally T H, Aubert J P, Batra S K. Retinoic acid-dependent transforming growth factor-beta 2-mediated induction of MUC4 mucin expression in human pancreatic tumor cells follows retinoic acid receptor-alpha signaling pathway [In Process Citation]. J Biol Chem 2000; 275:33929–33936.

REFERENCES FOR EXAMPLE II

1. Greenlee R T, Murray T, and Bolden, SWPA. Cancer Statistics, 2000. CA Cancer J Clin 2000; 50: 7–33.
2. Parkin, D M, Pisani, P, and Ferlay, J. Global Cancer Statistics. CA Cancer J Clin 1999, 49: 33–64.
3. Rozenblum E, Schute M, Goggins M, et. al. Tumor-suppressive pathways in pancreatic carcinoma. Cancer Res.1997; 57: 1731–1734.
4. Vogelstein B, and Kinzler K W. The multistep nature of cancer. Trends Genet 1993; 9:138–141.
5. Fearon E R, and Vogelstein, B. A genetic model for colorectal tumorigenesis. Cell 1990; 61:759–767.
6. Hruban R H, and Wilentz R E. Pancreas. In: N. Weidner, R. J. Cote, S. Suster, and L. M. Weiss (eds.), Modern Surgical Pathology. Philadelphia: W. B. Saunders Co., in press, 2001.
7. Brat D J, Lillemoe K D, Yeo C J, et. al. Progression of pancreatic intraductal neoplasias (high-grade PanIN) to infiltrating adenocarcinoma of the pancreas. Am J Surg Pathol 1998; 22: 163–169.
8. Hruban R H, Adsay N V, Albores-Saavedra J et al. Pancreatic Intraepithelial Neoplasia: A new nomenclature and classification system for pancreatic duct lesions. Am J Surg Pathol 2001; 25: 579–586.
9. Kozuka S, Sassa R, Taki T, et. al. Relation of pancreatic duct hyperplasia to carcinoma. Cancer 1979; 42: 1418–1428.
10. Pour P M, Sayed S, and Sayed G. Hyperplastic, pre-neooplastic and neoplastic lesions found in 83 human pancreases. Am J Clin Pathol 1982; 77: 147–152.
11. Furukawa T, Chiba R, Kobari M, et. al. Varying grades of epithelial atypia in the pancreatic ducts of humans. Classification based on morphometry and multivariate analysis and correlated with positive reactions of carcinoembryonic antigen. Arch Pathol Lab Med 1994; 118: 227–234.
12. Moskaluk C A, Hruban, R H, and Kern S E. p16 and K-ras gene mutations in the intraductal precursors of human pancreatic adenocarcinoma. Cancer Res 1997; 57: 2140–2143.
13. Wilentz R E, Geradts J, Maynard R, et. al. Inactivation of the p16 (INK4A) tumor-suppressor gene in pancreatic duct lesions: loss of intranuclear expression. Cancer Res 1998; 58: 4740–4744.
14. DiGiuseppe J A, Hruban R H, Goodman S M, et. al. Overexpression of p53 protein in adenocarcinoma of the pancreas. Am J Clin Pathol 1994; 101: 684–688.
15. Day J D, DiGiuseppe J A, Yeo C J, et. al. Immunohistochemical evaluation of HER-2/neu oncogene expression in pancreatic adenocarcinoma and pancreatic intraepithelial neoplasms. Hum Pathol 1996; 27: 119–124.
16. Yanagisawa A, Ohtake K, Ohashi K, et. al. Frequent c-Ki-ras oncogene activation in mucous cell hyperplasias of pancreas suffering from chronic inflammation. Cancer Res 1993; 53: 953–956.
17. Tada M, Ohashi M, Shiratori Y, et. al. Analysis of K-ras gene mutation in hyperplastic duct cells of the pancreas without pancreatic disease. Gastroenterology 1996; 110: 227–231.
18. Caldas C, Hahn S A, Hruban R H, et. al.. Detection of K-ras mutations in the stool of patients with pancreatic adenocarcinoma and pancreatic ductal hyperplasia. Cancer Res 1994; 54: 3568–3573.
19. Hameed M, Marrero A M, Conlon K C, et. al. . Expression of p53 nucleophosphoprotein in in situ pancreatic ductal adenocarcinoma: an immunohistochemical analysis of 100 cases. Lab. Invest 1994; 70: 132A.
20. Wilentz R E, Su G H, Dai J L et. al. Immunohistochemistry labeling for Dpc4 mirrors genetic status in pancreatic and peripancreatic adenocarcinomas: a new marker of DPC4 inactivation. Am J Pathol 2000; 156: 37–43.
21. Luttges J, Schlehe B. Menke M A, et al. The K-ras mutation pattern in pancreateic ductal adenocarcinoma usially is identical to that in associated normal hyperplastic, metaplastic ductal epithelium Cancer 1999 85:1703–1710.
22. Balaguè C, Gambùs G, Carrato C, et. al. Altered Expression of MUC2, MUC4, and MUC5 mucin genes in pancreas tissues and cancer cell lines, Gastroenterology 1994; 106: 1054–1061.
23. Andrianifahanana M, Moniaux N, Ringel J, et. al. MUCin (Muc) gene expression in human pancreatic adenocarcinoma and chronic pancreatitis: a potential role of MUC4 as a tumor marker of diagnostic significance. Proceedings of the AACR 2001; 42: 1727.
24. Balaguè C, Audiè J, Porchet N, et. al. In situ hybridization shows distinct patterns of mucin gene expression in normal, benign, and malignant pancreas tissues. Gastroenterology 1995; 109: 953–964.
25. Zhang S, Zhang H S, Cordon-Cardo C, et. al. Selection of tumor antigens as targets for immune attack using immunohistochemistry: protein antigens. Clin Cancer Res 1998; 4: 2669–2676.
26. Wilentz R E, Iacobuzio-Donahue C A, Argani, P, et. al. Loss of expression of Dpc4 in pancreatic intraepithelial neoplasia: evidence that DPC4 inactivation occurs late in neoplastic progression. Cancer Res 2000; 60: 2001–2006.
27. Luttges J, Zamboni G, Longnecker D, et. al. The immunohistochemical mucin expression pattern distinguishes different types of intraductal papillary mucinous neoplasms of the pancreas and determines their relationship to mucinous noncystic carcinoma and ductal adenocarcinoma. Am J Surg Pathol 2001; 25: 942–8.
28. Choudhury A, Moniauz N, Winpenny J P, et. al. Human MUC4 mucin cDNA and its variants in pancreatic carcinoma. J Biochem 2000; 128: 233–243.
29. Yonezawa S, Sato E. Expression of mucin antigens in human cancers and its relationship with malignancy potential. Pathology International 1997; 47: 813–330.
30. Choudhury A, Singh R K, Moniauz N et. al. Retinoic acid-dependent transforming growth factor-β2-mediated induction of MUC4 mucin expression in human pancreatic tumor cells follows retinoic acid receptor-α signaling pathway. J Biol Chem 2000; 275: 33929–33936.
31. Audie J P, Janin A, Porchet N, et. al. Expression of human mucin genes in respiratory, digestive, and reproductive tracts ascertained by in situ hybridization. J Histochem Cytochem 1993; 41:1479–1485.
32. Audie J P, Tetaert D, Pigny P, et. al. Mucin gene expression in the human endocervix. Hum Reprod 1995; 10: 98–102.
33. Gipson I. K, Spurr-Michaud S, Moccia R, et. al. MUC4 and MUC5B transcripts are the prevalent mucin messenger ribonucleic acids of the human endocervix. Biol. Reprod 1999; 60: 58–64.
34. Buisine M P, Devisme L, Copin M C, et. al. Developmental mucin gene expression in the human respiratory tract. Am J Respir Cell Mol Biol 1999; 20: 209–218.
35. Reid C J, and Harris A. Developmental expression of mucin genes in the human gastrointestinal system. Gut 1998; 42: 220–226.
36. Ringel J, Faulman G, Brandt R, et. al. MUC4 mRNA in peripheral blood mononuclear cells (PBMC) as a potential tumor marker for pancreatic cancer. Proceedings of the AACR, 42, 3311, March 2001.
37. Mehes G, Witt A, Kubista E, et. al. Circulating breast cancer cells are frequently apoptotic. Am J Pathol 2001; 159: 17–20.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting pancreatic cancer in a patient, said method comprising:
   a) providing at least a first and second biological sample, said first sample being obtained from said patient, and said second sample being obtained from a healthy subject for use as a negative control;
   b) isolating the peripheral blood mononuclear cells from said first and second samples;
   c) contacting said isolated peripheral blood mononuclear cells with an antibody or fragment thereof having binding affinity for MUC4, such that MUC4 antibody-peripheral blood mononuclear cell complexes or MUC4 antibody fragment-peripheral blood mononuclear cell complexes form if MUC4 is present; and
   d) detecting said complexes by a method selected from the group consisting of labeled primary antibody detection, labeled secondary antibody detection, flow cytometric analysis, immunochemical detection, radioimmunoassy, fluorescent immunoassay, enzyme-linked immunoassay, and immunoblot analysis;

wherein the presence of said complexes is indicative of pancreatic cancer in said patient.

2. The method of claim 1, wherein said antibody or fragment thereof having binding affinity for MUC4 comprises a label selected from the group consisting of fluorescein, rhodamine, phycoerythrin, biotin, and strepavidin.

3. The method of claim 1 wherein said antibody or fragment is in solution.

4. The method of claim 1 wherein said antibody or antibody fragment is immobilized on a solid support.

5. The method of claim 4, wherein said solid support is selected from the group consisting of filter paper, multiwell dishes, microchips, and derivatized magnetic particles.

6. The method of claim 1, wherein said peripheral blood mononuclear cells in said sample are T-cells.

7. A kit for performing the method of claim 1, said kit comprising:
  a) an antibody or fragment thereof having binding affinity for MUC4;
  b) detectable label for said antibody or fragment thereof;
  c) Ficoll-Paque for isolating peripheral blood mononuclear cells from whole blood; and
  d) reagents suitable for detecting MUC4-antibody immunocomplexes, if present in said biological sample.

8. The kit as claimed in claims 7, wherein said antibody or fragment thereof is in solution.

9. The kit as claimed in claim 7, wherein said antibody is immobilized on a solid support.

10. The kit as claimed in claim 9, wherein said solid support is selected from the group consisting of filter paper, multiwell dishes, microchips, and derivatized magnetic particles.

11. The kit as claimed in claim 7, wherein said detectable label is selected from the group consisting of fluorescein, rhodamine, phycoerythrin, biotin, and strepavidin.

12. The kit as claimed in claim 7, optionally comprising reagents suitable for flow cytometric analysis, immunochemical detection and immunoblot analysis.

13. The method of claim 1 comprising isolation of the MUC4 antibody-peripheral blood mononuclear cell complexes or MUC4 antibody fragment-peripheral blood mononuclear cell complexes.

* * * * *

SEQUENCE LISTING

<160> NUMBER OF SEQ ID NOS: 29

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
catcgtggct aaacaggtac tg                                    22

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gcacgacctt gagggcagcc                                       20

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
cgcggtggtg gaggcgttct t                                     21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gaagaatcct gacagccttc a                                     21

<210> SEQ ID NO 5
<211> LENGTH: 21
<212> TYPE: DNA
<213> ORGANISM: Artificial Sequence -continued

```
<220> FEATURE:
<223> OTHER INFORMATION: Primer

<400> SEQUENCE: 5
acgttccacg gaggagtgag g                                           21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ccttcccttt tccagtctcc c                                           21

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
gaactacggg cagctggaca tc                                          22

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gctctctggg ccagtcctcc t                                           21

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
ctgcaccaag accgtcctca tg                                          22

<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10
gcaaggactg aacaaagact cagac                                       25

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
agtccacgtt gaccaccact gc                                          22
```

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tgttcacatc ctggctggcg                                                   20

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tgatcatcca gcagcagggc t                                                 21

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
ccgagctcag aggacatatg gg                                                22

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
ctgcgagacc gaggtcaaca tc                                                22

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tgggcagcag gagcacggag                                                   20

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gcatggcgaa cgtgacggta a                                                 21

<210> SEQ ID NO 18
<211> LENGTH: 22
<212> TYPE: DNA
<213> ORGANISM: Artificial Sequence
<220> FEATURE:
<223> OTHER INFORMATION: Primer

```
<400> SEQUENCE: 18
tagtctgagc ccctgcttgg ca                                              22

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ccacacctaa ttcttcccca actac                                           25

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
ctggcttgtg ggatagaggc att                                             23

<210> SEQ ID NO 21
<211> LENGTH: 18
<212> TYPE: DNA
<213> ORGANISM: Artificial Sequence
<220> FEATURE:
<223> OTHER INFORMATION: Primer

<400> SEQUENCE: 21
ctcatcagcg aggactgg                                                   18

<210> SEQ ID NO 22
<211> LENGTH: 18
<212> TYPE: DNA
<213> ORGANISM: Artificial Sequence
<220> FEATURE:
<223> OTHER INFORMATION: Primer

<400> SEQUENCE: 22
cagggctgcc tgctgcag                                                   18

<210> SEQ ID NO 23
<211> LENGTH: 18
<212> TYPE: DNA
<213> ORGANISM: Artificial Sequence
<220> FEATURE:
<223> OTHER INFORMATION: Primer

<400> SEQUENCE: 23
cccactgcgg ggtcagga                                                   18

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
gggtcttgtt ggcgttgta                                                  19

<210> SEQ ID NO 25
```

```
<211> LENGTH: 22
<212> TYPE: DNA
<213> ORGANISM: Artificial Sequence
<220> FEATURE:
<223> OTHER INFORMATION: Primer

<400> SEQUENCE: 25
catcgtggct aaacaggtac tg                                              22

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gcacgacctt gagggcagcc                                                 20

<210> SEQ ID NO 27
<211> LENGTH: 16
<212> TYPE: PRT
<213> ORGANISM: Homo sapiens

<400> SEQUENCE: 27

Ser Thr Gly Asp Thr Thr Pro Leu Pro Val Thr Asp Thr Ser Ser Val
 1               5                  10                  15

<210> SEQ ID NO 28
<211> LENGTH: 14
<212> TYPE: PRT
<213> ORGANISM: Homo sapiens

<400> SEQUENCE: 28

Ala Thr Tyr Arg Pro Pro Gln Pro Ala Trp Met Phe Gly Asp
 1               5                  10

<210> SEQ ID NO 29
<211> LENGTH: 15
<212> TYPE: PRT
<213> ORGANISM: Homo sapiens

<400> SEQUENCE: 29

Gly Ala Arg Phe Ser Tyr Phe Leu Asn Ser Ala Glu Ala Leu Pro
 1               5                  10                  15
```